US006726708B2

(12) United States Patent
Lasheras

(10) Patent No.: US 6,726,708 B2
(45) Date of Patent: Apr. 27, 2004

(54) THERAPEUTIC HEATING AND COOLING VIA TEMPERATURE MANAGEMENT OF A COLON-INSERTED BALLOON

(75) Inventor: Juan C. Lasheras, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 09/881,175

(22) Filed: Jun. 14, 2001

(65) Prior Publication Data
US 2002/0004675 A1 Jan. 10, 2002

Related U.S. Application Data
(60) Provisional application No. 60/211,406, filed on Jun. 14, 2000.

(51) Int. Cl.$^7$ .................................................. A61F 7/00
(52) U.S. Cl. .................... 607/105; 607/104; 606/21; 606/22
(58) Field of Search .................... 607/96, 104, 105, 607/113, 114; 606/20, 21, 22, 27

(56) References Cited

U.S. PATENT DOCUMENTS

| | | | |
|---|---|---|---|
| 1,011,606 A | * | 12/1911 | Fulton ........................... 606/21 |
| 2,058,780 A | * | 10/1936 | Elliott ........................... 607/105 |
| 2,148,541 A | * | 2/1939 | Dierker ........................... 606/21 |
| 2,308,484 A | | 1/1943 | Auzin et al. |
| 2,374,609 A | | 4/1945 | McCollum |
| 2,466,042 A | * | 4/1949 | Reich et al. .................... 606/21 |
| 2,615,686 A | | 10/1952 | Davidson |
| 2,672,032 A | | 3/1954 | Towse |
| 2,913,009 A | | 11/1959 | Kuthe |
| 3,087,493 A | | 4/1963 | Schossow |
| 3,125,096 A | * | 3/1964 | Antiles ........................... 606/21 |
| 3,298,371 A | | 1/1967 | Lee |
| 3,425,419 A | | 2/1969 | Dato |
| 3,504,674 A | | 4/1970 | Swenson et al. |
| 3,604,419 A | | 9/1971 | Diskin et al. |
| 3,768,484 A | * | 10/1973 | Gawura ........................ 604/909 |
| 3,809,520 A | | 5/1974 | Wilk et al. |
| 3,865,116 A | | 2/1975 | Brooks |
| 3,888,259 A | | 6/1975 | Miley |
| 3,971,383 A | | 7/1976 | Van Gerven |
| 4,038,519 A | | 7/1977 | Foucras |
| 4,153,048 A | | 5/1979 | Magrini |
| 4,160,455 A | | 7/1979 | Law |
| 4,190,033 A | | 2/1980 | Foti |
| 4,231,425 A | | 11/1980 | Engstrom |
| 4,275,734 A | | 6/1981 | Mitchiner |

(List continued on next page.)

FOREIGN PATENT DOCUMENTS

| | | |
|---|---|---|
| EP | 0655225 A1 | 5/1993 |
| EP | 0 664 990 | 11/1997 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |

(List continued on next page.)

OTHER PUBLICATIONS

Mercer and Jessen, "Effects of Total Body Core Cooling on Heat Production of Conscious Goats".
Jessen et al. "Intravascular Heat Exchanger for Conscious Goats".
Gerbrandy et al. "Oral, Rectal, and esophageal temperatures in relation to central temperature control in man".
White; *Cerebral Hypothermia and Circulatory Arrest*; Jul. 1978; pp. 450–458; Mayo Clinic Proceedings, vol. 53.

(List continued on next page.)

Primary Examiner—Roy D. Gibson
(74) Attorney, Agent, or Firm—Karin L. Williams; Mayer Fortkort & Williams; Mark D. Wieczorek

(57) ABSTRACT

A method and apparatus is provided for heating or cooling at least a selected portion of a patient's body. The method begins by inserting a catheter having a balloon into the colon or stomach of the patient. A heated or chilled fluid is conducted through a supply lumen of the catheter and into the balloon. The fluid is evacuated from the balloon through a return lumen of the catheter.

21 Claims, 5 Drawing Sheets

U.S. PATENT DOCUMENTS

| | | | |
|---|---|---|---|
| 4,298,006 A | 11/1981 | Parks | |
| 4,318,722 A | 3/1982 | Altman | |
| 4,427,009 A | 1/1984 | Wells et al. | |
| 4,445,500 A | 5/1984 | Osterholm | |
| 4,483,341 A | 11/1984 | Witteles | |
| 4,502,286 A | 3/1985 | Okada et al. | |
| 4,569,355 A | 2/1986 | Bitterly | |
| 4,581,017 A | 4/1986 | Sahota | |
| 4,655,746 A | 4/1987 | Daniels et al. | |
| 4,672,962 A | 6/1987 | Hershenson | |
| 4,748,979 A | 6/1988 | Hershenson | |
| 4,750,493 A | 6/1988 | Brader | |
| 4,762,129 A | 8/1988 | Bonzel | |
| 4,762,130 A | 8/1988 | Fogarty et al. | |
| 4,820,349 A | 4/1989 | Saab | |
| 4,860,744 A | 8/1989 | Johnson et al. | |
| 4,883,455 A | 11/1989 | Leonard | |
| 4,894,164 A | 1/1990 | Polaschegg | |
| 4,904,237 A | 2/1990 | Janese | |
| 4,920,963 A | 5/1990 | Brader | |
| 4,964,409 A | 10/1990 | Tremulis | |
| 5,000,734 A | 3/1991 | Boussignac | |
| 5,002,531 A | 3/1991 | Bonzel | |
| 5,014,695 A | 5/1991 | Benak et al. | |
| 5,018,521 A | 5/1991 | Campbell | |
| 5,019,075 A | 5/1991 | Spears et al. | |
| 5,041,089 A | 8/1991 | Mueller et al. | |
| 5,059,057 A | 10/1991 | Graef | |
| 5,078,713 A | 1/1992 | Varney | |
| 5,084,044 A * | 1/1992 | Quint | 606/27 |
| 5,092,841 A | 3/1992 | Spears | |
| 5,106,360 A | 4/1992 | Ishiwara et al. | |
| 5,108,390 A | 4/1992 | Potocky et al. | |
| 5,110,721 A | 5/1992 | Anaise et al. | |
| 5,117,822 A | 6/1992 | Laghi | |
| 5,147,355 A | 9/1992 | Friedman et al. | |
| 5,149,321 A | 9/1992 | Klatz et al. | |
| 5,150,706 A | 9/1992 | Cox et al. | |
| 5,151,100 A | 9/1992 | Abele et al. | |
| 5,190,539 A | 3/1993 | Fletcher et al. | |
| 5,191,883 A | 3/1993 | Lennox et al. | |
| 5,195,965 A * | 3/1993 | Shantha | 607/105 |
| 5,196,024 A | 3/1993 | Barath | |
| 5,211,631 A | 5/1993 | Sheaff | |
| 5,234,405 A | 8/1993 | Klatz et al. | |
| 5,241,951 A | 9/1993 | Mason et al. | |
| 5,248,312 A | 9/1993 | Langberg | |
| 5,250,070 A | 10/1993 | Parodi | |
| 5,257,977 A | 11/1993 | Eshel | |
| 5,264,260 A | 11/1993 | Saab | |
| 5,267,341 A | 11/1993 | Shearin | |
| 5,269,369 A | 12/1993 | Faghri | |
| 5,269,749 A | 12/1993 | Koturov | |
| 5,269,758 A | 12/1993 | Taheri | |
| 5,281,213 A | 1/1994 | Milder et al. | |
| 5,281,215 A | 1/1994 | Milder | |
| 5,310,440 A | 5/1994 | Zingher | |
| 5,330,519 A | 7/1994 | Mason et al. | |
| 5,334,193 A | 8/1994 | Nardella | |
| 5,342,301 A | 8/1994 | Saab | |
| 5,344,436 A | 9/1994 | Fontenot et al. | |
| 5,365,750 A | 11/1994 | Greenthal | |
| 5,368,591 A | 11/1994 | Lennox et al. | |
| 5,383,918 A | 1/1995 | Panetta | |
| 5,395,314 A | 3/1995 | Klatz et al. | |
| 5,395,331 A | 3/1995 | O'Neill et al. | |
| 5,403,281 A | 4/1995 | O'Neill et al. | |
| 5,417,686 A | 5/1995 | Peterson et al. | |
| 5,423,745 A | 6/1995 | Todd et al. | |
| 5,423,807 A | 6/1995 | Milder | |
| 5,433,740 A | 7/1995 | Yamaguchi | |
| 5,437,673 A | 8/1995 | Baust et al. | |
| 5,462,521 A | 10/1995 | Brucker et al. | |
| 5,486,204 A | 1/1996 | Clifton | |
| 5,486,208 A | 1/1996 | Ginsburg | |
| 5,496,311 A * | 3/1996 | Abele et al. | 606/28 |
| 5,531,776 A | 7/1996 | Ward et al. | |
| 5,549,559 A * | 8/1996 | Eshel | 604/113 |
| 5,554,119 A | 9/1996 | Harrison et al. | |
| 5,558,644 A | 9/1996 | Boyd et al. | |
| 5,573,532 A | 11/1996 | Chang et al. | |
| 5,578,008 A | 11/1996 | Hara | |
| 5,584,804 A | 12/1996 | Klatz et al. | |
| 5,588,438 A | 12/1996 | McKown et al. | |
| 5,591,162 A | 1/1997 | Fletcher et al. | |
| 5,617,854 A | 4/1997 | Munsif | |
| 5,620,480 A | 4/1997 | Rudie | |
| 5,624,392 A | 4/1997 | Saab | |
| 5,647,051 A | 7/1997 | Neer | |
| 5,709,654 A | 1/1998 | Klatz et al. | |
| 5,713,941 A | 2/1998 | Robins et al. | |
| 5,716,386 A | 2/1998 | Ward et al. | |
| 5,735,809 A | 4/1998 | Gorsuch | |
| 5,797,878 A | 8/1998 | Bleam | |
| 5,800,480 A | 9/1998 | Augustine et al. | |
| 5,800,493 A * | 9/1998 | Stevens et al. | 606/28 |
| 5,807,391 A | 9/1998 | Wijkamp | |
| 5,824,030 A | 10/1998 | Yang et al. | |
| 5,827,222 A | 10/1998 | Klatz et al. | |
| 5,827,237 A | 10/1998 | Macoviak et al. | |
| 5,827,269 A | 10/1998 | Saadat | |
| 5,833,671 A | 11/1998 | Macoviak et al. | |
| 5,837,003 A | 11/1998 | Ginsburg | |
| 5,861,021 A | 1/1999 | Thome et al. | |
| 5,868,735 A * | 2/1999 | Lafontaine | 606/21 |
| 5,871,526 A | 2/1999 | Gibbs et al. | |
| 5,873,835 A | 2/1999 | Hastings et al. | |
| 5,879,329 A | 3/1999 | Ginsburg | |
| 5,891,094 A | 4/1999 | Masterson et al. | |
| 5,899,899 A | 5/1999 | Arless et al. | |
| 5,902,268 A | 5/1999 | Saab | |
| 5,913,856 A | 6/1999 | Chia et al. | |
| 5,913,885 A | 6/1999 | Klatz et al. | |
| 5,913,886 A | 6/1999 | Soloman | |
| 5,916,242 A | 6/1999 | Schwartz | |
| 5,957,963 A | 9/1999 | Dobak, III | |
| 5,989,238 A | 11/1999 | Ginsburg | |
| 6,019,783 A | 2/2000 | Philips et al. | |
| 6,033,383 A | 3/2000 | Ginsburg | |
| 6,096,068 A | 8/2000 | Dobak, III et al. | |
| 6,126,684 A | 10/2000 | Gobin et al. | |
| 6,146,411 A | 11/2000 | Noda et al. | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak, III | |
| 6,165,207 A | 12/2000 | Balding et al. | |
| 6,231,594 B1 | 5/2001 | Dae | |
| 6,261,312 B1 | 7/2001 | Dobak, III et al. | |
| 6,270,494 B1 | 8/2001 | Kovalcheck et al. | |
| 6,454,792 B1 * | 9/2002 | Noda et al. | 607/105 |
| 6,641,602 B2 * | 11/2003 | Balding | 607/105 |
| 2001/0001832 A1 | 5/2001 | Dobak, III et al. | |
| 2001/0005791 A1 | 6/2001 | Ginsburg et al. | |
| 2001/0039440 A1 | 11/2001 | Lasheras et al. | |
| 2002/0068877 A1 | 6/2002 | Abramovitch et al. | |
| 2002/0151943 A1 | 10/2002 | Balding | |

FOREIGN PATENT DOCUMENTS

| | | |
|---|---|---|
| WO | WO 96/40347 | 12/1996 |
| WO | WO 97/01374 | 1/1997 |

| | | |
|---|---|---|
| WO | WO 97/25011 | 7/1997 |
| WO | WO 98/26831 | 6/1998 |
| WO | WO 98/31312 | 7/1998 |
| WO | WO 00/09054 | 2/2000 |
| WO | WO 00/10494 | 3/2000 |
| WO | WO 00/38601 | 7/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/76655 | 10/2001 |

OTHER PUBLICATIONS

Yenari; *Thrombolysis with Tissue Plasminogen Activator (TPA) is Temperature Dependent*; Jul. 1994; pp. 475–481; Thrombosis Research, vol. 77, No. 5.

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, N. 2.

Shiraki, K., et al.; "Esophageal and Tympanic Temperature Responses to Core Blood Temperature Changes During Hyperthermia"; American Physiological Society; Department of Physiology, School of Medicine, University of Occupational and Environmental Health, Kitakyushu 807, Japan; pp. 98–102; (1986).

Deklunder, G., et al; "Influence of the Face on Thermoregulation in Man During Hyper– and Hypothermia"; European Journal of Applied Physiology and Occupational Physiology; 62: 342–348; (1991).

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stroke Model*; Feb. 1994; pp. 131–138; Brain Research, vol. 647.

Milleret, Rene; *La cryo–chirurgie danes les varices des mimbres inferieurs*; Angiologie; Supplement au No. 110.

Milleret; Abstract of *Cryosclerosis of the Saphenous Veins in Varicose Reflux in the Obese and Elderly*; 10.1981; one page; Phlebologie, vol. 34, No. 4.

Parkins; *Brain Cooling in the Prevention of Brain Damage During Periods of Circulatory Occlusion in Dogs*; Apr. 1954; pp. 284–289; Annals of Surgery, vol. 140, No. 3.

Piepgras; *Rapid Active Internal Core Cooling for Induction of Moderate Hypothermia in Head Injury by Use of an Extracorporeal Heat Exchanger*; Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Schwartz, A.E. et al.; (1996); *Isolated cerebral hypothermia by single carotid artery perfusion of extracorporeally cooled blood in baboons*; Neurosurgery 39(3):577–582.

Schwartz; *Cerebral Blood Flow during Low–flow Hypothermic Cardiopulmonary Bypass in Baboons*; Oct. 1994; pp. 959–964; Anesthesiology, vol. 81, No. 4.

Schwartz; *Selective Cerebral Hypothermia by Means of Transfemoral Internal Carotid Artery Catheterization*; May 1996; pp. 571–572; Radiology, vol. 201, No. 2.

Steen; *The Detrimental Effects of Prolonged Hypothermia and Rewarming in the Dog*; Aug. 1979; pp. 224–230; Anesthesiology, vol. 52, No. 3.

Vandam; *Hypothermia*; Sep. 1959; pp. 546–553; The New England Journal of Medicine.

Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.

Bigelow; *Hypothermia, Its Possible Role in Cardiac Surgery*; Nov. 1959; pp. 849–866; Annals of Surgery, vol. 132, No. 5.

Cheatle; *Cryostripping the Long and Short Saphenous Veins*; Aug. 1993; one page; Br. J. Surg., vol. 80; 1283.

Dexter; *Blood Warms as It Blows Retrograde from a Femoral Cannulation Site to the Carotid Artery During Cardiopulmonary Bypass*; Nov. 1994; pp. 393–397; Perfusion, vol. 9, No. 6.

Gillinov; *Superior Cerebral Protection with Profound Hypothermia During Circulatory Arrest*; Nov. 1992; pp. 1432–1439; Ann. Thorac. Surg., vol. 55.

Higazi; *The Effect of Ultrasonic Irradiation and Temperature on Fibrinolytic Activity in Vitro*; Aug. 1992; p. 251–253; Thrombosis Research, vol. 69, No. 2.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

Jos R.C. Jansen, Ph.D., et al. (1997) *Near continuous cardiac output by thermodilution*. Journal of Clinical Monitoring 13:233–239.

Kimoto; *Open Heart Surgery under Direct Vision with the Aid of Brain–Cooling by Irrigation*; Jul. 1955; pp. 592–603; Surgery, vol. 39, No. 4.

Marekovic, Z.; *Abstract of Renal Hypothermia in Situ by Venous Passages: Experimental Work on Dogs*; 1980; Eur Urol 6(2); 1 page.

\* cited by examiner

THERAPEUTIC HEATING AND COOLING VIA TEMPERATURE MANAGEMENT OF A COLON-INSERTED BALLOON

RELATED APPLICATIONS

This application is a continuation-in-part of U.S. Appl. Ser. No. 60/211,406, entitled "THERAPEUTIC HEATING AND COOLING VIA TEMPERATURE MANAGEMENT OF A COLON-INSERTED BALLOON," filed in the United States Patent and Trademark Office on Jun. 14, 2000.

BACKGROUND OF THE INVENTION

I. Field of the Invention

The present invention relates generally to the modification and control of the temperature of the body. More particularly, the invention relates to a method for controlling body temperature by heat transfer to a balloon.

II. Description of the Related Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Patients may require pre or post-operative cooling for a variety of reasons, including, for example, treatment of a malignant hypothermia crisis and induction of therapeutic hypothermia for neurosurgery.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato invention is directed towards a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel.

Other less cumbersome catheters have been developed to provide cooling intravascularly. For example, a heat transfer element such as disclosed in U.S. Pat. No. 6,096,068, incorporated herein by reference in its entirety, may be placed in the feeding artery of an organ to absorb or deliver the heat from or to the blood flowing into the organ. The transfer of heat may cause either a cooling or a heating of the selected organ. The heat transfer element is small enough to fit within the feeding artery while still allowing a sufficient blood flow to reach the organ in order to avoid ischemic organ damage. By placing the heat transfer element within the feeding artery of an organ, the temperature of the organ can be controlled with less of an effect on the temperature of the remaining parts of the body. A similar heat transfer device, which is employed for whole body cooling and which may be disposed in the venous vasculature, is disclosed in U.S. application Ser. No. 09/373,112, also incorporated by reference in its entirety.

While the previously mentioned techniques provide significant thermal control, they require the insertion of a catheter into the vascular system to induce heat transfer between the catheter and the blood stream. This is a relatively invasive procedure, which has an associated level of risk.

Accordingly, it would be desirable to provide an effective, less invasive method and apparatus for heating or cooling all or part of a patient's body. It would also be desirable to provide an effective, less invasive method and apparatus for heating or cooling all or part of a patient's body that could be employed in emergency situations, such as on an ambulance.

SUMMARY OF THE INVENTION

The present invention provides a method and apparatus for heating or cooling at least a selected portion of a patient's body. The invention provides a method and device to transfer heat to or from the at least a selected portion in an efficient manner. The device has a high degree of flexibility and is collapsible, thereby affording an easy insertion procedure. The device allows a high surface area to increase heat transfer.

The method begins by inserting a balloon catheter through the anus into the colon of the patient. The system includes a supply lumen and an at least partially inflatable return lumen. The return lumen is coupled to the supply lumen so as to transfer working fluid between the two. A heated or chilled fluid is conducted through the supply lumen of the catheter and into the balloon. The fluid is evacuated from the balloon through the return lumen of the catheter. Heat transfer occurs between the working fluid and the tissue of the colon.

Variations of the system may include one or more of the following. The supply lumen and the return lumen may be made of a flexible material such as latex rubber or other plastics. The radii of the supply and return lumens may decrease in a distal direction such that the supply and return lumens are tapered when inflated. A wire may be disposed in the supply or return lumens to provide shape and strength when deflated.

The thickness of the return lumen, when inflated, may be less than about ½ mil. The length of the supply lumen may be between about 5 and 150 or more centimeters.

The system may further include a coaxial supply catheter having an inner catheter lumen coupled to the supply lumen and a working fluid supply configured to dispense the working fluid and having an output coupled to the inner catheter lumen. The working fluid supply may be configured to produce a pressurized working fluid at a temperature of between about −3° C. and 50° C. Higher or lower temperatures may be employed if desired.

In another aspect, the invention is directed to a method of changing the temperature of a body by heat transfer. The method includes inserting an inflatable heat transfer element into the colon of a patient and inflating the same by delivering a working fluid to its interior. The temperature of the working fluid is generally different from that of the colon tissue. The flexible, conductive heat transfer element preferably absorbs more than about 500 watts of heat.

The circulating may further include passing the working fluid in through a supply lumen and out through a return, coaxial lumen. The working fluid may be a liquid at or well below its boiling point, and furthermore may be aqueous.

Advantages of the invention include one or more of the following. The design criteria described above for the heat transfer element: small diameter when deflated, large diameter when inflated, high flexibility, and enhanced heat transfer rate through increases in the surface of the heat transfer element facilitate creation of a heat transfer element which successfully achieves patient cooling or heating. The process is relatively non-invasive. In addition, rapid cooling or heating to a precise temperature may be achieved. Further, treatment of a patient is not cumbersome and the patient may easily receive continued care during the heat transfer process. The device and method may be easily combined with other devices and techniques to provide aggressive multiple therapies. The device may employ the ubiquitous saline as a working fluid. The device has a very high surface area, particularly as the length may be on the order of a meter and the diameter on the order of 0.1 meters. Use of the device may not require the sedation of the patient. The power transferred during cooling could be as high as 600 to 1000 watts. Other advantages will become clear from the description below, including the figures and claims, as well as from the above.

BRIEF DESCRIPTION OF THE SEVERAL VIEWS OF THE DRAWINGS

The novel features, objects, and advantages of the invention will become more apparent from the detailed description set forth below when taken in conjunction with the drawings in which like reference characters identify corresponding elements throughout.

FIG. 2 being an expanded view;

DETAILED DESCRIPTION OF THE INVENTION

Figure 1:
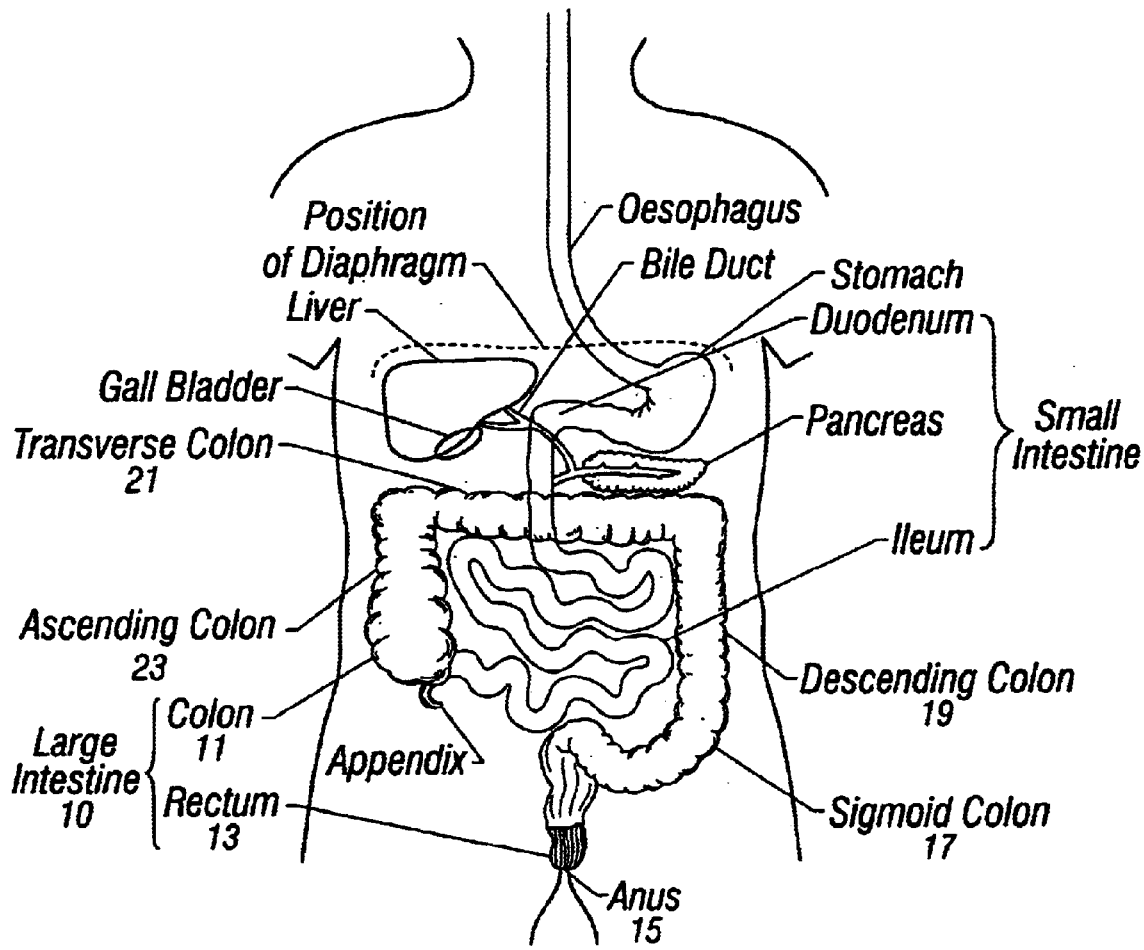
FIGS. 1 and 2 show schematic diagrams of the digestive tract.

The present invention provides a relatively non-intrusive method and apparatus for heating or cooling all or part of a patient's body. The invention achieves this result by circulating a heat transfer fluid through a balloon (not shown in FIG. 1) disposed in a patient's colon 11 (see FIG. 1). The colon 11 forms part of the large intestine 10. The rectum 13 forms the remaining part of the large intestine 10. The final stage in the digestive process is passage through the anus 15. The colon 11 has four parts: the ascending colon 23, the transverse colon 21, the descending colon 19, and the sigmoid colon 17. Various other components are also shown in FIG. 1.

Figure 2:
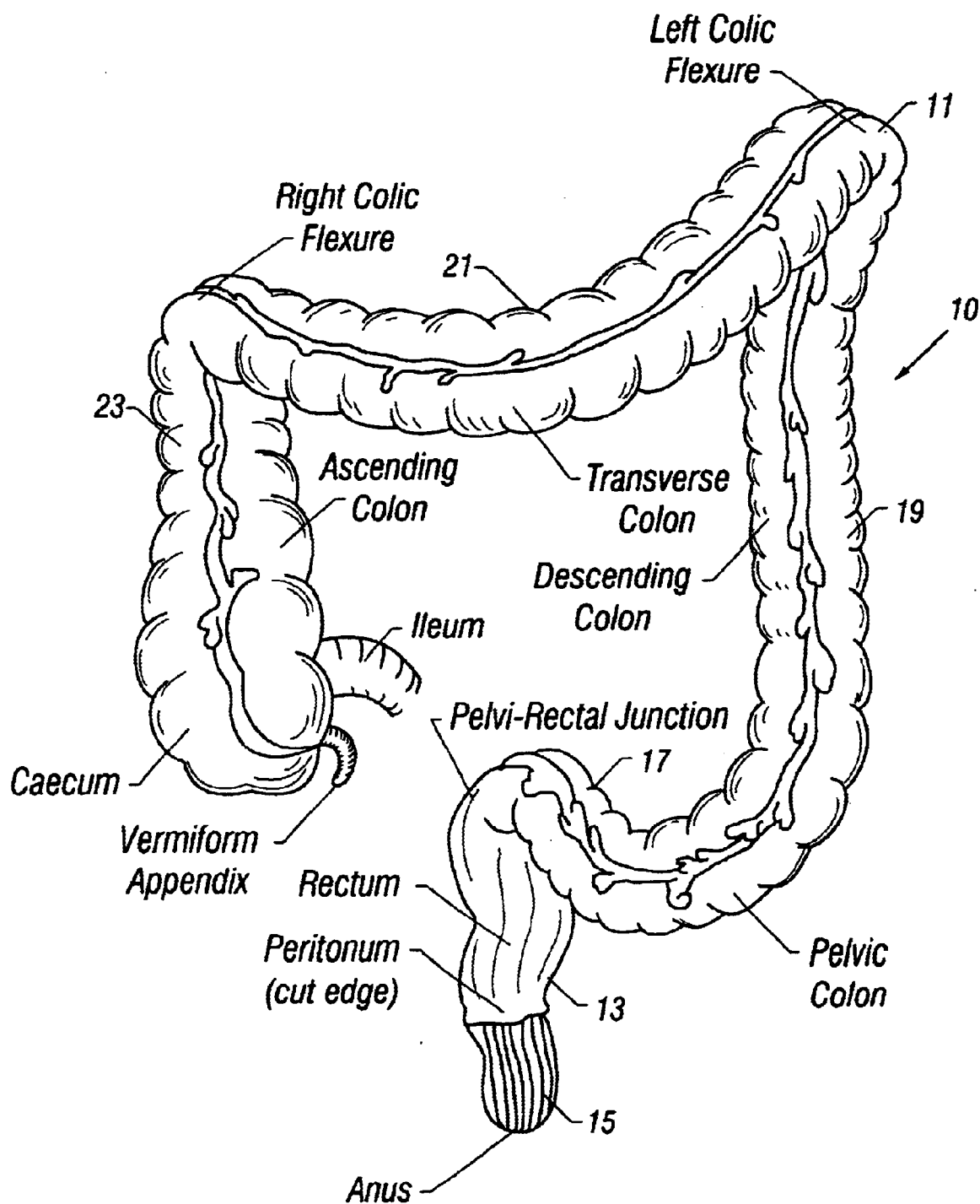

FIG. 2 shows an enlarged view of the large intestine 10 and colon 11.

Heat transfer via the colon 11 is advantageous because the colon 11 is located in the abdominal cavity, is surrounded by a variety of organs, and in addition the tissues of the colon walls may be highly perfused with blood. Further, the abdominal cavity volume includes a substantial portion of the high blood flow vessels the aorta and the inferior vena cava. The working fluid absorbs heat from or delivers heat through the wall of the colon 11 and into the abdominal cavity and the arterial and venous vessels populating this area, thereby regulating the temperature of a patient's whole body or one or more selected organs. As a result, cooling of the internal organs and a considerable amount of blood can be accomplished without the invasive step of inserting a catheter directly into the vascular system.

The mechanism of heat transfer into and out of the catheter is via conduction. Once the tissue of the colon has a modified temperature, the mechanism of heat transfer may be via convection through the blood as well as by conduction through the tissue.

Figure 3:
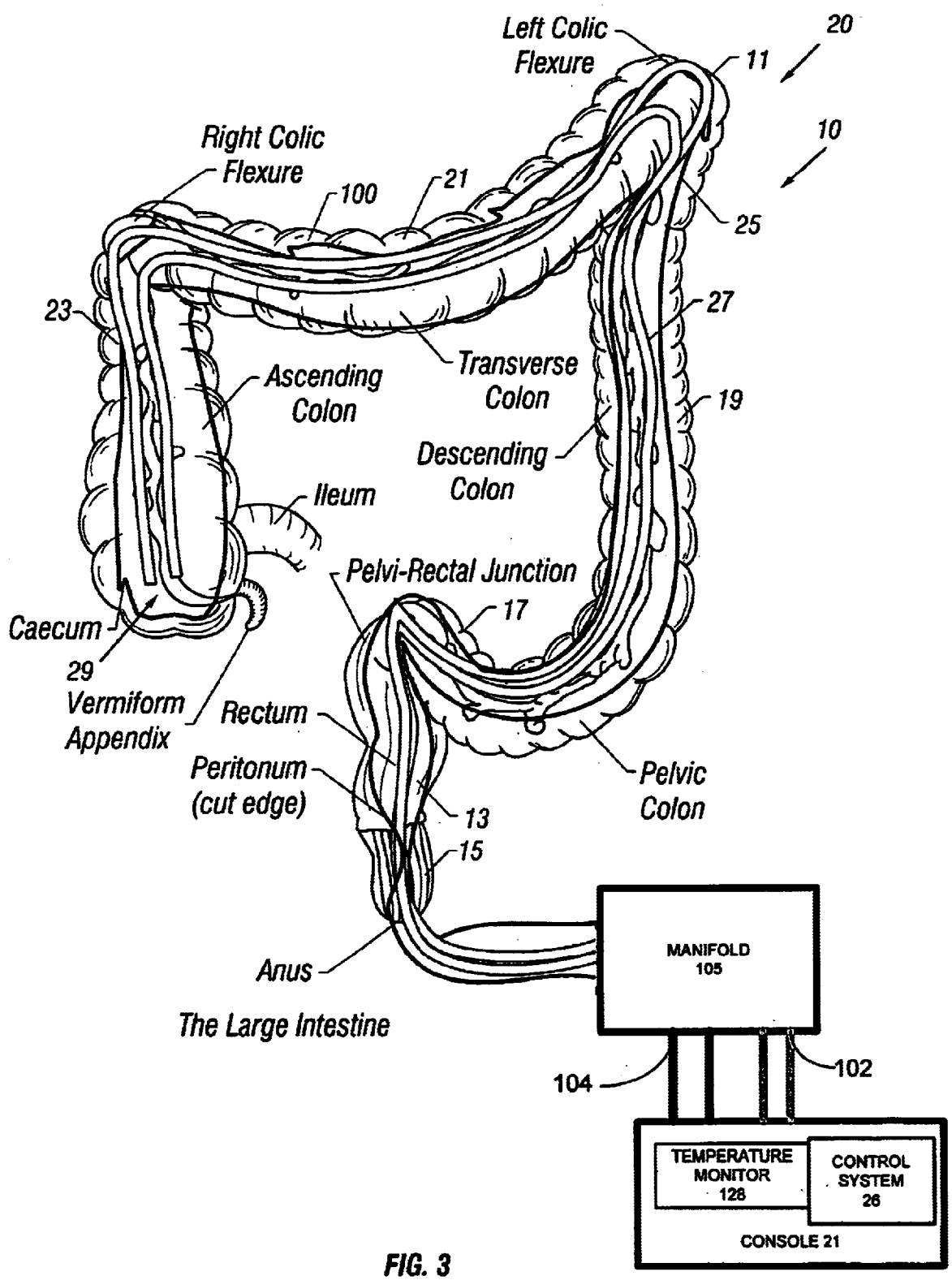
FIG. 3 shows a schematic diagram of a device according to an embodiment of the invention.

FIG. 3 shows one embodiment of the colon thermal control system constructed in accordance with the present invention. The system includes a catheter 100, a control system 26, and a circulation set (not shown) partially housed by a console 21. The control system 26 may be equipped with an output display and input keys to facilitate user interaction. The core body temperature may be determiend by a temperature monitor 128, which may be an esophageal monitor, a tympanic monitor, or any other type of temperature monitor as is known in the art with which core body temperature may be monitored. The complexity of the console 21 depends on the application to which the same is put. For example, for a rewarming application, the console 21 may be a simple Mallinkrodt Blood and Fluid Warmer, as manufactured by Mallinkrodt Medical of St. Louis, Mo.

In the same way, for certain applications, such as for rewarming or maintaining normothermia during a surgery or other procedure, the nature of the heat exchanger used within the control system may be simple, such as a simple resistive heat exchanger or thermo-electric heat exchanger.

The catheter 100, which may employ a design similar to that of a large balloon catheter, for example, is configured for insertion into the colon. The proximal end of the catheter 100 includes a manifold 105 having an inlet port 102 and an outlet port 104 on its proximal end. The supply lumen 27 and the return lumen 25 are connected to a port located on the distal end of the manifold 105. At the catheter's distal end the supply and return lumens are fluidly coupled via an orifice 29. The catheter may have an inflated diameter of, e.g., 1–10 cm or another size as dictated by the requirements of the user.

The catheter 100 may be made of a very soft material so as to minimize tissue damage of the colon and other organs upon insertion. The same may be coated with various materials to minimize deleterious coating of undesired biological materials on the tip during or after insertion.

The supply and return lumens may be formed from a pair of concentric flexible tubes so that the supply lumen may be concentrically located within the annular return lumen. Of course, the same may also be non-coaxial as dictated by the requirements of the user. As shown in FIG. 3, when the catheter 100 is properly inserted into the colon its distal end may be located in the ascending colon 23. Fluid is conducted into the balloon, i.e., inflatable return lumen 25, from the supply lumen 27 via orifice 29.

As in a conventional Foley catheter for the urethra, the catheter 100 may include an additional anchoring balloon (not shown) near its proximal end to prevent its expulsion from the colon. The anchoring balloon may also serve the purpose of anchoring the catheter against movement caused by a pulsating working fluid supply, as may be the case if certain types of pumps are employed to drive the working fluid. The anchoring balloon may be inflated by a single inflation lumen, a dual inflation lumen, or other such lumen as are known.

The circulation set and console may include any of the features of such systems described in co-pending applications: Ser. No. 60/247,203, filed Nov. 7, 2000, entitled "Improved Circulation Set for Temperature Controlled Catheter and Method of Using Same", and Ser. No. 09/827,010, filed Apr. 5, 2001, entitled "Method and Apparatus for Regulating Patient Temperature by Irrigating the Bladder with a Fluid", both of which are incorporated herein by reference in their entirety. These applications disclose one or more of the following: a fluid reservoir, a pump, a filter, a heat exchanger, a temperature and pressure sensor assembly, a supply line, and a return line. The supply line and return line are preferably comprised of one or more pieces of tubing, connectors, etc. joining the aforementioned components of the circulation set. The circulation set supplies, filters, circulates, and monitors the temperature and pressure of the heat transfer fluid for the catheter 100.

The pressure inside the balloon is preferably not higher than about 10 psi, and may be about 0 to 3 psi.

In one embodiment, the fluid reservoir is a modified IV bag made of PVC filled with saline. Considering the heat transfer expected, the flow rate of the saline may be about 10 to 100 cc/sec, or even higher. The temperature of the saline may vary such that in a cooling mode, the saline is maintained between about 0° C. and 5° C., whereas in heating the same is maintained between about 40° C. and 42° C. Other fluids may also be used according to the requirements of the user.

The fluid reservoir is used to prime the lines of the circulation set and the lumens of the catheter 100. For example, the system may be primed with 0.9% saline, and then the pump speed adjusted appropriately.

The heat exchanger, which is used to heat or chill the fluid supplied to the catheter, may be any of a variety of conventionally designed heat exchangers. As noted above, the heat exchanger may employ a resistive heater, a microwave heater, a thermoelectric device, a closed-circuit temperature control system, etc.

The temperature and pressure sensor assembly may include alarms that shut down the system if a dangerous situation arises. For example, a maximum safe temperature of working fluid may be about 50° C. If this temperature were exceeded, the system may be designed to shut itself down or even turn itself off. Alternatively, a high temperature may be allowed, but only for a short predetermined period of time insufficient to cause tissue damage.

A control system may be provided to accept a temperature feedback signal and to control the temperature of the working fluid thereby. Of course, it is noted that the location of the catheter 100, in the abdominal cavity, may have an associated time delay with respect to the patient temperature due to the slow mechanism of heat transfer (conduction) through the colon walls. Such a time lag may be expected to be about 10 to 20 minutes.

The fluid may be provided to the supply lumen in a continuous, constant flow or as a pulsed flow of fluid. The pulsed flow may be a flow that is either intermittently interrupted or simply reduced in rate on an intermittent basis. For example, the flow rate may be pulsed at a frequency of every few minutes. The present invention also contemplates more complex flow rate patterns such as periodic and aperiodic oscillatory patterns.

As the insertion of a rectal-type catheter is generally uncomplicated, and can be performed by nurses or emergency personnel, embodiments of the invention may be implemented on an emergency vehicle such as an ambulance. One aspect allowing this may be inclusion in certain embodiments of a compressed gas system to cool a circulating fluid. It is again noted that in heating embodiments a simple resistive heater may be employed.

Figure 4A:
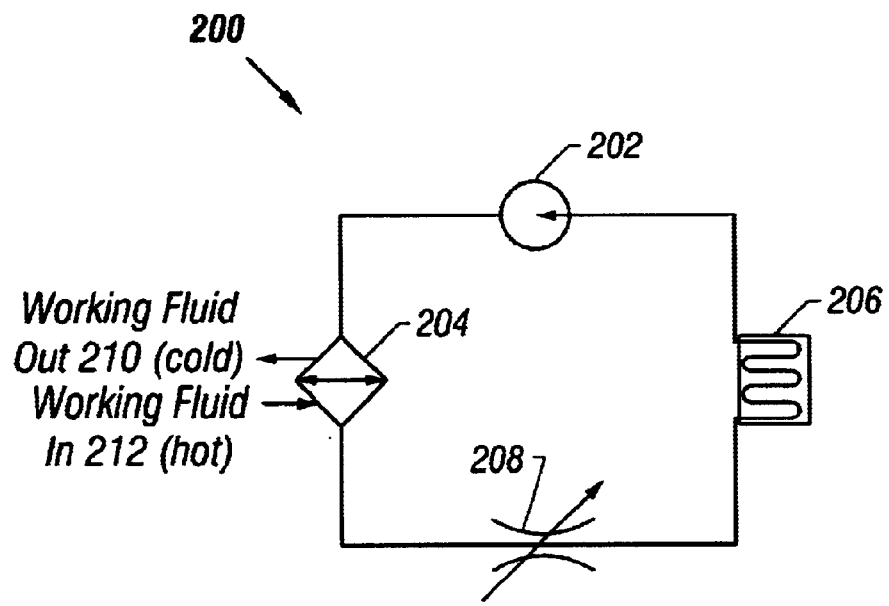
FIG. 4A shows a prior art heat exchange system.

Prior chiller units employing a closed cycle evaporative gas system were complicated, expensive, and difficult to simplify and miniaturize for use in a portable transportable system. Further, they required significant electrical power to operate. For example, referring to FIG. 4A, a prior art refrigeration system 200 is shown. Such a system is exceedingly well known, and includes a pump 202, a heat exchanger 204, a restriction valve 208, and an apparatus 206 to exhaust heat to a temperature bath. In this system, as is known, a liquid to gas heat exchanger transfers heat from the working fluid to the cold side of an evaporative chiller.

Figure 4B:
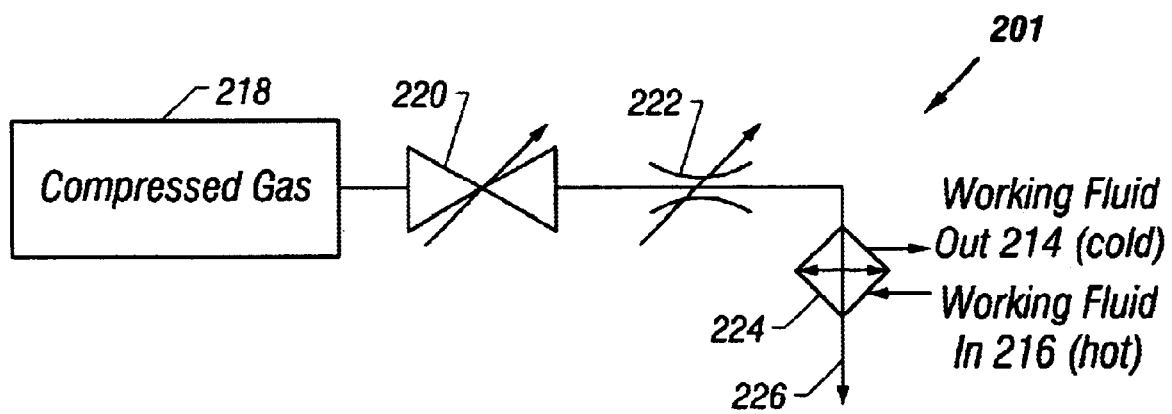
FIG. 4B shows a heat exchange system constructed in accordance with an embodiment of the invention.

A system 201 according to an embodiment of the present invention is shown in FIG. 4B. In this figure, a source of compressed gas 218 is valvably coupled via valve 220 to an optional restriction valve 222 to a heat exchanger 224. A working fluid output for, e.g., cold working fluid, is labeled by outlet 214. A working fluid input for, e.g., hot working fluid, is labeled by inlet 216. An exhaust to the environment is shown as exhaust 226.

In system 201, a compressed gas from source 218 is expanded adiabatically through a valve. The expansion results in a reduced temperature gas that absorbs heat from the working fluid in the liquid-to-gas heat exchanger 224. The heated, expanded gas is then discarded to the environment via exhaust 226. An additional temperature reduction in the expanded gas may be achieved by the phase change from the storage pressure to the expanded pressure.

Gases which may be useful in embodiments of the invention employing adiabatic expansion include nitrogen, carbon dioxide, etc. Gases which may be useful in embodiments of the invention employing adiabatic expansion with a phase change include nitrous oxide.

Figure 5A:
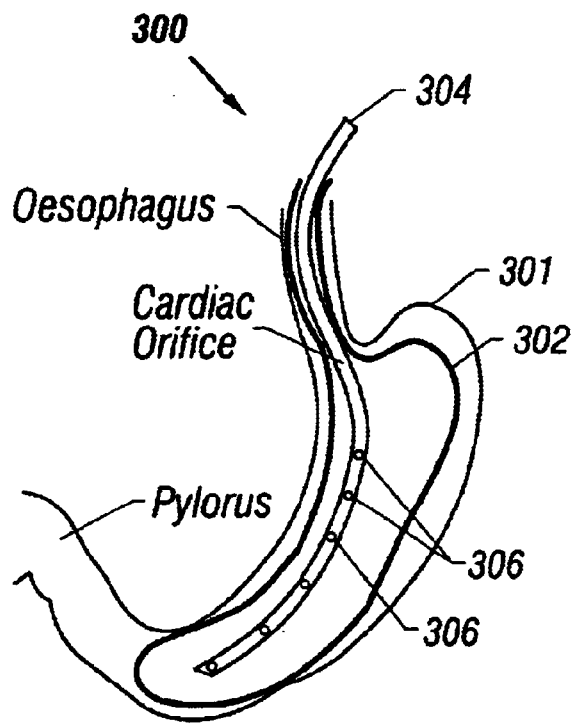
FIGS. 5A and 5B show embodiments of an alternative embodiment of the invention in use within the stomach, showing both deflated and inflated states.
Figure 5B:
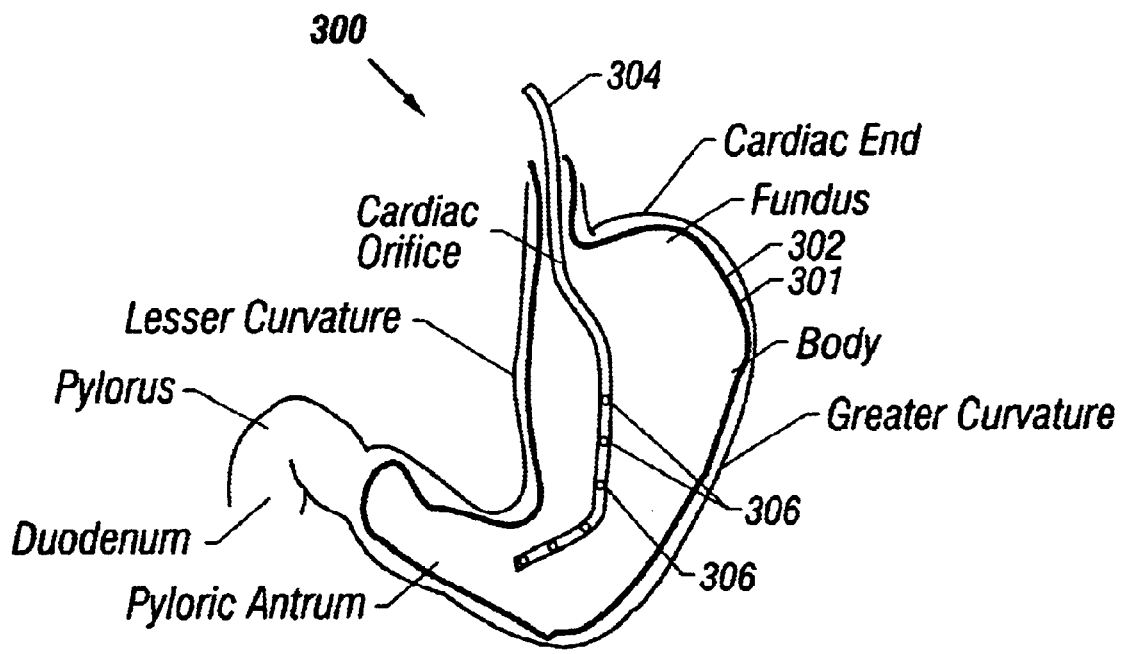

Referring to FIGS. 5A and 5B, it should also be clear to one of skill in the art given the teaching herein that an analogous balloon 300 may be located in the stomach 301 to cool or heat that organ and thus the vasculature surrounding the stomach, leading to temperature management of all or a portion of the patient. A plurality of longitudinally spaced working fluid exits 306 may be disposed along a supply lumen 304 that is placed within a return lumen 302 having the approximate shape of a stomach 301. In such a way, the return lumen 302 when inflated takes the approximate shape of the stomach to enhance heat transfer. The temperature and pressure requirements of this embodiment may be approximately the same as that in the colon embodiment, although obviously this embodiment would be inserted through the esophagus. This embodiment may have the further advantage of being in close proximity to the liver, lungs, as well as other major arteries and veins. Thus, convection can rapidly become a major component of heat transfer and it is expected that power of up to or in excess of 1000 watts can be transferred.

While the invention herein disclosed is capable of obtaining the objects hereinbefore stated, it is to be understood that this disclosure is merely illustrative of the presently preferred embodiments of the invention and that no limitations are intended other than as described in the appended claims. For example, the invention can be used in a wide variety of settings, e.g., in the applications of general surgery, and in particular lengthy surgeries, orthopedic and back surgery, liver transplants, etc. Further, suction may be implemented on the return lumen in order to maintain even lower pressures inside the balloon, particularly when the flow rate of working fluid is increased to 10–200 cc/s. A guide wire may be used to place the catheter 100 in the desired location. While the colon embodiment shown spans the ascending, transverse, and descending colons for maximum power transferred, lower power requirements may be met by placing the catheter in less than the entire colon.

What is claimed is:

1. A method for heating or cooling at least a selected portion of a body, comprising:
   inserting a catheter into the colon, the catheter including a supply lumen and a return lumen;
   conducting a heated or chilled fluid through the supply lumen of the catheter; and
   evacuating the fluid from the catheter through to return lumen,
   wherein the fluid is conducted into the supply lumen with a periodically interrupted flow of fluid.

2. A method for heating or cooling at least a selected portion of a body, comprising:
   inserting a catheter into the colon, the catheter including a supply lumen and a return lumen;
   conducting a heated or chilled fluid through the supply lumen of the catheter;
   evacuating the fluid from the catheter through the return lumen; and
   monitoring a temperature differential between the fluid conducted into the supply lumen and the fluid flowing through the return lumen.

3. A method for heating or cooling at least a selected portion of a body, said method comprising:
   inserting a catheter into the stomach, the catheter including a supply lumen and a return lumen;
   conducting a heated or chilled fluid through the supply lumen of the catheter;
   evacuating the fluid from the catheter through the return lumen; and
   monitoring a temperature differential between the fluid conducted into the supply lumen and die fluid flowing through the return lumen.

4. A method for heating or cooling at least a selected portion of a body, said method comprising:
   irrigating a balloon inserted into the colon with a heated or chilled fluid;
   controlling at least one measurable parameter of the fluid irrigating the balloon;
   evacuating the fluid from the balloon; and
   monitoring, during the irrigation step, the at least one measurable parameter of fluid flowing out of the balloon,
   wherein irrigating the balloon includes the step of irrigating the balloon with a pulsed flow of fluid.

5. The method of claim 4, further comprising maintaining the pressure of the heated or chilled fluid in the balloon to between about 0 and 10 psi.

6. The method of claim 5, further comprising maintaining the pressure of the heated or chilled fluid in the balloon to between about 0 and 3 psi.

7. The method of claim 4, wherein the conducting includes delivering the heated or chilled fluid at a substantially constant rate.

8. The method of claim 7, wherein the substantially constant rate is between about 0 and 200 cc/sec.

9. The method of claim 4 wherein the at least one measurable parameter is selected from the group consisting of the flow rate of the fluid, the pressure differential between the fluid flowing into and out of the balloon, and the temperature differential between the fluid flowing into and out of the balloon.

10. A method for heating or cooling at least a selected portion of a body, said method comprising:
    irrigating a balloon inserted into the colon with a heated or chilled fluid;
    controlling at least one measurable parameter of the fluid irrigating the balloon;
    evacuating the fluid from the balloon;
    monitoring, during the irrigation step, the at least one measurable parameter of fluid flowing out of the balloon; and
    controlling a temperature, flow rate, or pressure of the heated or chilled fluid based on a monitored pressure.

11. An apparatus for heating or cooling at least a selected portion of a body, comprising:
    a catheter for irrigating and evacuating a balloon for insertion into the colon with a heated or chilled fluid;
    means, coupled to the catheter, for controlling at least one measurable parameter of the fluid irrigating the balloon; and
    means for monitoring at least one parameter selected from the group consisting of:
       the at least one measurable parameter of fluid flowing out of the balloon while it is being irrigated and a core temperature of the body,
       wherein the at least one measurable parameter is the pressure differential between the fluid flowing into and out of the balloon.

12. The apparatus of claim 11, wherein the flow of the fluid is continuous.

13. The apparatus of claim 11, further comprising means for monitoring a temperature differential between the fluid flowing into and out of the balloon.

14. The apparatus of claim 11, wherein said catheter includes a supply lumen having an orifice at its distal end.

15. The apparatus of claim 14, wherein said catheter further includes a return lumen, said return lumen being fluidically coupled to said supply lumen via said orifice.

16. A catheter, comprising:
    a manifold having a proximal end with at least first and second input ports and a distal end with an output port;
    at least first and second flexible tubes defining a supply lumen and a return lumen, respectively, said first and second flexible tubes configured and structured for insertion into the colon and having proximal ends removably connectable to the output port of the manifold and having distal ends fluidically coupled via an orifice,
    wherein said first and second flexible tubes are concentrically oriented with respect to one another.

17. The catheter of claim 16, further comprising an inflatable balloon coupled to said catheter for maintaining an operative position of said catheter when inserted into a patient.

18. The catheter of claim 16, further comprising
    a gas-driven heat exchanger for chilling a working fluid.

19. The catheter of claim 16, further comprising
    a resistive heater for heating a working fluid.

20. The catheter of claim 16, further comprising a means for monitoring a core temperature of the body, and wherein the means is an esophageal temperature monitor.

21. The catheter of claim 16, further comprising a means for monitoring the core temperature of the body, and wherein the means is a tympanic temperature monitor.

* * * * *